United States Patent [19]

Gaffar et al.

[11] Patent Number: 5,192,530
[45] Date of Patent: Mar. 9, 1993

[54] ANTIBACTERIAL ANTIPLAQUE ORAL COMPOSITION

[75] Inventors: Abdul Gaffar, Princeton; Nuran Nabi, No. Brunswick; John Afflitto, Brookside, all of N.J.; Orum Stringer, Yardley, Pa.

[73] Assignee: Colgate-Palmolive Company, New York, N.Y.

[21] Appl. No.: 754,887

[22] Filed: Sep. 6, 1991

Related U.S. Application Data

[63] Continuation of Ser. No. 398,606, Aug. 25, 1989, abandoned, which is a continuation-in-part of Ser. No. 291,712, Dec. 29, 1988, Pat. No. 4,894,220, and a continuation-in-part of Ser. No. 346,258, May 1, 1989, Pat. No. 5,043,154, each is a continuation-in-part of Ser. No. 8,901, Jan. 30, 1987, abandoned.

[51] Int. Cl.$^5$ .......................... A61K 7/16; A61K 7/18
[52] U.S. Cl. ......................................... 424/52; 424/49
[58] Field of Search ................................. 424/49–58

[56] References Cited

U.S. PATENT DOCUMENTS

| | | | |
|---|---|---|---|
| 3,003,988 | 10/1961 | Germann et al. | 524/474 |
| 3,629,477 | 12/1971 | Model | 424/370 |
| 3,736,274 | 5/1973 | Schoenholz et al. | 523/120 |
| 3,878,138 | 4/1975 | Keegan et al. | 523/120 |
| 3,919,357 | 11/1975 | Keegan et al. | 106/35 |
| 3,936,402 | 2/1976 | Keegan et al. | 106/35 |
| 4,209,434 | 6/1980 | Wilson et al. | 106/35 X |
| 4,315,779 | 2/1982 | Heyd et al. | 106/35 |
| 4,360,605 | 11/1982 | Schmitt et al. | 523/116 |
| 4,373,036 | 2/1983 | Chang et al. | 523/118 |
| 4,393,080 | 7/1983 | Pawelchak et al. | 523/118 |
| 4,485,090 | 11/1984 | Chang | 424/52 |
| 4,511,486 | 4/1985 | Shah | 252/90 |
| 4,514,528 | 4/1985 | Dhabhar et al. | 523/120 |
| 4,521,551 | 6/1985 | Chang et al. | 523/120 |
| 4,569,954 | 2/1986 | Wilson et al. | 523/116 |
| 4,569,954 | 2/1986 | Wilson et al. | 523/116 |
| 4,569,955 | 2/1986 | Dhabhar | 523/120 |
| 4,608,088 | 8/1986 | Lokken | 523/120 |
| 4,678,436 | 7/1987 | Kondo et al. | 106/35 X |
| 4,689,080 | 8/1987 | Kawahara | 106/35 |
| 4,719,149 | 1/1988 | Aasen et al. | 106/35 X |
| 4,725,576 | 2/1988 | Pollock et al. | 514/2 |
| 4,749,562 | 6/1988 | Lang et al. | 424/49 |
| 4,758,630 | 7/1988 | Shah et al. | 523/120 |
| 4,879,136 | 11/1989 | Pölz | 106/35 X |
| 4,880,660 | 11/1989 | Aasen et al. | 106/35 X |
| 4,883,534 | 11/1989 | Sandham et al. | 106/35 |
| 4,886,843 | 12/1989 | Walton | 523/116 X |
| 4,894,220 | 1/1990 | Gappar et al. | 424/52 |
| 4,990,394 | 2/1991 | Shoher et al. | 106/35 X |
| 4,997,699 | 3/1991 | Shoher et al. | 106/35 X |
| 5,023,107 | 6/1991 | Roberts | 523/116 X |

FOREIGN PATENT DOCUMENTS

| | | | |
|---|---|---|---|
| 128655 | 12/1984 | European Pat. Off. | 424/54 |
| 140766 | 5/1985 | European Pat. Off. | 424/49 |
| 161899 | 11/1985 | European Pat. Off. | |
| 223545 | 5/1987 | European Pat. Off. | 424/49 |
| 264660 | 4/1988 | European Pat. Off. | 424/54 |
| 271332 | 6/1988 | European Pat. Off. | |
| 89/10736 | 11/1989 | PCT Int'l Appl. | 424/54 |
| 1495255 | 12/1977 | United Kingdom | 424/54 |

OTHER PUBLICATIONS

Reed, et al. CA 108:11023j (1988).
Jones, et al. CA. 108:10197r (1988).
Jackson, CA. 108:137715e (1988).
Gaffar, et al. CA. 109:215788t (1988).
Caserio, CA. 110:160260c (1989).
Moran, CA. 111:63740x (1989).
Jenkins, CA. 111:140181v (1989).
Addy, CA. 111:159965a (1989).
Wagner, CA. 107:204966g (1982).
Gilbert, CA. 107:102430k (1982).
Gilbert, CA. 107:46041v (1982).
Lane, et al. CA.106:107776s (1987).
Gilbert, CA. 106:38214t (1987).
Saxton, CA. 104:135881z (1986).
Vinson, CA. 87:29036y (1977).
Model, CA. 77:30329w (1972).

*Primary Examiner*—Shep K. Rose
*Attorney, Agent, or Firm*—Robert L. Stone; Murray M. Grill

[57] ABSTRACT

An oral composition dentifrice comprising an orally acceptable vehicle, about 5–30% by weight of a siliceous polishing agent, a substantially water-insoluble noncationic antibacterial antiplaque agent, such as 2,4,4'-trichloro-2'-hydroxydiphenyl ether (triclosan), and an antibacterial-enhancing agent which enhances the delivery of said antibacterial agent to, and retention thereof on, oral surfaces, wherein said antiplaque agent is substantially completely dissolved in saliva present during tooth and gum cleaning in a solubilizing agent therefor. The solubilizing agent may be a humectant polyol such as propylene glycol, dipropylene glycol and hexylene glycol; a cellosolve such as methyl cellosolve and ethyl cellosolve; a vegetable oil or wax containing at least about 12 carbon atoms in a straight chain such as olive oil, castor oil and petrolatum; or an ester such as ethyl acetate, amyl acetate, glyceryl tristearate and benzyl benzoate.

20 Claims, No Drawings

ANTIBACTERIAL ANTIPLAQUE ORAL COMPOSITION

This application is a continuation of application Ser. No. 07/398,606 filed Aug. 25, 1989, now abandoned, which is a continuation-in-part of application Ser. No. 07/291,712, filed Dec. 29, 1988, and now U.S. Pat. No. 4,894,220, and of application Ser. No. 07/346,258 filed May 1, 1989 and now U.S. Pat. No. 5,043,154 which are respectively a continuation-in-part and a continuation of application Ser. No. 07/008901, filed Jan. 30, 1987, now abandoned.

This invention relates to an antibacterial antiplaque oral composition dentifrice. More particularly, it relates to an oral composition dentifrice containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurence of gingivitis.

Accordingly, it is highly desirable to include antimicrobial agents which have been known to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogentated hydroxydiphenyl ethers. The noncationic antibacterial antiplaque halogentated hydroxydiphenyl ether, triclosan, has also been described in combination with zinc citrate trihydrate in European Patent Publication 0161,899 to Saxton et al.

The cationic antibacterial materials such as chlorhexidine, benzthonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

It is an advantage of this invention than an oral composition dentifrice containing a substantially water-insoluble noncationic antibacterial agent and an antibacterial-enhancing agent which enhances the delivery of said antibacterial agent to, and retention thereof on, oral surfaces is provided to inhibit plaque formation.

It is an advantage of this invention that said antibacterial-enhancing agents enhance the delivery and retention of the antibacterial agent on teeth and on soft oral tissues.

It is a further advantage of this invention that such an oral composition is provided with a solubilizing agent which dissolves the noncationic antibacterial agent for effective delivery onto soft oral tissues.

It is a further advantage of this invention that an antiplaque oral composition is provided which is effective to reduce the occurence of gingivitis.

Additional advantages of this invention will be apparent from consideration of the following specification.

In accordance with certain of its aspects, this invention relates to an oral composition dentifrice comprising in an orally acceptable vehicle, about 5–30% by weight of a siliceous polishing agent, an effective antiplaque amount of a substantially water insoluble noncationic antibacterial agent, and about 0.05–4% by weight of an antibacterial-enhancing agent which enhances the delivery of said antibacterial agent to, and retention thereof on, oral surfaces, wherein said oral composition comprises a solubilizing material for said antibacterial agent in amount sufficient to dissolve said antibacterial agent in saliva. Typical examples of water insoluble noncationic antibacterial agents which are particularly desirable from considerations of antiplaque effectiveness, safety and formulation are:

Halogenated Diphenyl Ethers
2′,4,4′-trichloro-2-hydroxy-diphenyl ether (Triclosan)
2,2′-dihydroxy-5,5′-dibromo-diphenyl ether.

Halogenated Salicylanilides
4′,5-dibromosalicylanilide
3,4′,5-trichlorosalcylanilide
3,4′,5-tribromosalicylanilide
2,3,3′,5-tetrachlorosalicylanilide
3,3,3′,5-tetrachlorosalicylanilide
3,5-dibromo-3′-trifluoromethyl salicylanilide
5-n-octanoyl-3′-trifluoromethyl salicylanilide
3,5-dibromo-4′-trifluoromethyl salicylanilide
3,5-dibromo-3′-trifluoro methyl salicylanilide (Flurophene)

Benzoic Esters
Methyl-p-Hydroxybenzoic Ester
Ethyl-p-Hydroxybenzoic Ester
Propyl-p-Hydroxybenzoic Ester
Butyl-p-Hydroxybenzoic Ester Halogenated Carbanilides
3,4,4′-trichlorocarbanilide
3-trifluoromethyl-4,4′-dichlorocarbanilide
3,3,4′-trichlorocarbanilide Phenolic Compounds (including phenol and its homologs, mono- and poly-alkyl and aromatic halo (e.g. F, Cl, Br, I)-phenols, resorcinol and catechol and their derivatives and bisphenolic compounds). Such phenolic compounds include inter alia:

Phenol and its Homologs
Phenol
2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n Propyl-Phenol
4-n-Butyl-Phenol
4-n-Amyl-Phenol
4-tert-Amyl-Phenol
4-n-Hexyl-Phenol
4-n-Heptyl-Phenol
2-Methoxy-4-(2-Propenyl)-Phenol (Eugenol)
2-Isopropyl-5-Methyl-Phenol (Thymol)
Mono- and Poly-Alkyl and Aralkyl Halophenols Methyl-p-Chlorophenol
Ethyl-p-Chlorphenol
n-Propyl-p-chlorophenol
n-Butyl-p-Chlorophenol
n-Amyl-p-chlorophenol
sec-Amyl-p-Chlorophenol
n-Hexyl-p-chlorophenol
Cyclohexyl-p-Chlorophenol
n-Heptyl-p-chlorophenol
n-Octyl-p-Chlorophenol
O-Chlorophenol
Methyl-o-chlorophenol
Ethyl-o-Chlorophenol
n-Propyl-o-Chlorophenol
n-Butyl-o-chlorophenol
n-Amyl-o-Chlorophenol
tert-Amyl-o-chlorophenol
n-Hexyl-o-chlorophenol
n-Heptyl-o-Chlorophenol
p-chlorophenol
o-Benzyl-p-Chlorophenol
o-Benzyl-m-methyl-p-Chlorophenol
o-Benzyl-m, m-dimethyl-p-Chlorophenol
o-Phenylethyl-p-Chlorophenol
o-Phenylethyl-m-methyl-p-Chlorophenol
-b 3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol
4-Chloro-2-methyl phenol
4-chloro-3-methyl phenol
4-chloro-3,5-dimethyl phenol
2,4-dichloro-3,5-dimethyl phenol
3,4,5,6-tetrabromo-2-methylphenol
5-methyl-2-pentylphenol
4-isopropyl-3-methylphenol
5-chloro-2-hydroxydiphenyl methane
  Resorcinol and Its Derivatives
Resorcinol
Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane
  Bisphenolic Compounds
Bisphenol A
2,2'-methylene bis (4-chlorophenol)
2,2'-methylene bis (3,4,6-trichlorophenol) (hexachlorophene)
2,2'-methylene bis (4-chloro-6-bromophenol)
bis (2-hydroxy-3,5-dichlorophenyl) sulfide
bis (2-hydroxy-5-chlorobenzyl) sulfide The noncationic antibacterial agent is present in the oral composition in an effective antiplaque amount, typically about 0.01-5% by weight, preferably about 0.03-1% and most preferably about 0.3-0.5%. The antibacterial agent is substantially water-insoluble, meaning that its solubility is less than about 1% by weight in water at 25° C. and may be even less than about 0.1%.

The preferred halogenated diphenyl ether is triclosan. The preferred phenolic compounds are phenol, thymol, eugenol, hexyl resorcinol and 2,2'methylene bis (4-chloro-6-bromophenol). The most preferred antibacterial antiplaque compound is triclosan. Triclosan is disclosed in aforementioned U.S. Pat. No. 4,022,880 as an antibacterial agent in combination with an anticalculus agent which provides zinc ions and in German Patent Disclosure 3,532,860 in combination with a copper compound. In European Patent Disclosure 0278744 it is disclosed in combination with a tooth desensitizing agent containing a source of potassium ions. It is also disclosed as an antiplaque agent in a dentifrice formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxton et al. In Europeon Patent Application 271332 a typical drug release system which could include triclosan in a toothpaste is described which contains a solubilizing agent such as propylene glycol.

AEA polymeric materials of the present invention include those which can be characterized as having utility as dentifrice adhesives or fixatives or dental cements. For example, U.S. Pat. Nos. 4,521,551 and 4,375,036, each to Chang et al, describe commercially available copolymer of methylvinyl ether-maleic anhydride (Gantrez) as a denture fixative. However, there has not been recognition in the prior art that adhesives, fixatives or cements when applied in water-soluble or water-swellable form together with substantially water-insoluble non-cationic antibacterial antiplaque agents could enhance the antibacterial activity of such agents. Further, in U.S. Pat. No. 4,485,090 to Chang, Gantrez AN copolymer is mentioned among polymeric anionic membrane-forming materials which attach to a tooth surface to form a hydrophobic barrier which reduces elution of a previously applied therapeutic caries prophylactic fluoride compound. Again, there is no recognition that such polymeric material could enhance the antibacterial activity of substantially water-insoluble non-cationic antibacterial antiplaque agents.

The antibacterial-enhancing agent (AEA) which enhances delivery of said antibacterial agent to, and retention thereof on, oral surfaces, is employed in amounts effective to achieve such enhancement within the range in the oral composition of about 0.05% to about 4%, preferably about 0.1% to about 3%, more preferably about 0.5% to about 2.5% by weight.

This AEA may be a simple compound, preferably a polymerizable monomer, more preferably a polymer, which latter term is entirely generic, including for example oligomers, homopolymers, copolymers of two or more monomers, ionomers, block copolymers, graft copolymers, cross-linked polymers and copolymers, and the like. The AEA may be natural or synthetic, and water insoluble or preferably water (saliva) soluble or swellable (hydratable, hydrogel forming). It has an (weight) average molecular weight of about 100 to about 1,000,000, preferably about 1,000 to about 1,000,000, more preferably about 2,000 or 2,500 to about 250,000 or 500,000.

The AEA ordinarily contains at least one delivery-enhancing group, which is preferably acidic such as sulfonic, phosphinic, or more preferably phosphonic or carboxylic, or salt thereof, e.g. alkali metal or ammonium, and at least one organic retention-enhancing group, preferably a plurality of both the delivery-enhancing and retention-enhancing groups, which latter groups preferably have the formula —(X)$_n$—R wherein X is O, N, S, SO, SO$_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired functions of the AEA as enhancing the delivery of the antibacterial agent to, and retention thereof on, oral surfaces such as halo, e.g. Cl, Br, I, and carbo and the like. Illustrations of such enhancing groups are tabulated below.

| n | X | —(X)$_n$R |
|---|---|---|
| 0 | — | methyl, ethyl, propyl, butyl, isobutyl, t-butyl, cyclohexyl, allyl, benzyl, phenyl, chlorophenyl, xylyl, pyridyl, furanyl, acetyl, benzoyl, butyryl, terephthaloyl, etc. |
| 1 | O | ethoxy, benzyloxy, thioacetoxy, phenoxy, carboethoxy, carbobenzyloxy, etc. |
|   | N | ethylamino, diethylamino, propylamido, benzylamino, benzoylamido, phenylacetamido, etc. |
|   | S | thiobutyl, thioisobutyl, thioallyl, thiobenzyl, thiophenyl, thiopropionyl, phenylthioacetyl, thiobenzoyl, etc. |
|   | SO | butylsulfoxy, allylsulfoxy, benzylsulfoxy, phenylsulfoxy, etc. |
|   | SO$_2$ | butylsulfonyl, allylsulfonyl, benzylsulfonyl, phenylsulfonyl, etc. |
|   | P | diethyphosphinyl, ethylvinylphosphinyl, ethylallylphosphinyl, ethylbenzylphosphinyl, ethylphenylphosphinyl, etc. |
|   | PO | diethylphosphinoxy, ethylvinylphosphinoxy, methylallylphosphinoxy, methylbenzyphosphinoxy, methylphenylphosphinoxy, etc. |
|   | Si | trimethysilyl, dimethylbutylsilyl, dimethylbenzylsilyl, dimethylvinylsilyl, dimethylallylsilyl, etc. |

As employed herein, the delivery-enhancing group refers to one which attached or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

Preferably, the AEA is an anionic polymer comprising a chain or backbone containing repeating units each preferably containing at least one carbon atom and preferably at least one directly or indirectly pendant, monovalent delivery-enhancing group and at least one directly or indirectly pendant monovalent retention-enhancing group geminally, vicinally or less preferably otherwise bonded to atoms, preferably carbon, in the chain. Less preferably, the polymer may contain delivery-enhancing groups and/or retention-enhancing groups and/or other divalent atoms or groups as links in the polymer chain instead of or in addition to carbon atoms, or as cross-linking moieties.

It will be understood that any examples or illustrations of AEA's disclosed herein which do not contain both delivery-enhancing groups and retention enhancing groups may and preferably should be chemically modified in known manner to obtain the preferred AEA's containing both such groups and preferably a plurality of each such groups. In the case of the preferred polymeric AEA's, it is desirable, for maximizing substantivity and delivery of the antibacterial agent to oral surfaces, that the repeating units in the polymer chain or backbone containing the acidic delivery enhancing groups constitute at least about 10%, preferably at least about 50%, more preferably at least about 80% up to 95% or 100% by weight of the polymer.

According to a preferred embodiment of this invention, the AEA comprises a polymer containing repeating units in which one or more phosphonic acid delivery-enhancing groups are bonded to one or more carbon atoms in the polymer chain. An example of such an AEA is poly (vinyl phosphonic acid) containing units of the formula:

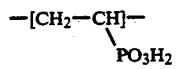   I which however does not contain a retention-enhancing group. A group of the latter type would however be present in poly (1-phosphonopropene) with units of the formula:

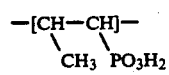   II

A preferred phosphonic acid-containing AEA for use herein is poly (beta styrene phosphonic acid) containing units of the formula:

$$-[CH-CH]- \quad \text{III}$$
$$\quad\ \ \ \backslash\quad\ \ \backslash$$
$$\quad\ \ \ Ph\quad PO_3H_2$$

wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of the foregoing formula III alternating or in random association with units of formula I above, or poly (alpha styrene phosphonic acid) containing units of the formula:

$$-[CH_2-C\text{------}]- \quad \text{IV}$$
$$\quad\ \ \ /\ \backslash$$
$$\quad\ \ Ph\quad PO_3H_2$$

in which the delivery- and retention-enhancing groups are geminally bonded to the chain.

These styrene phosphonic acid polymers and their copolymers with other inert ethylenically unsaturated monomers generally have molecular weights in the range of about 2,000 to about 30,000, preferably about 2,500 to about 10,000. Such "inert" monomers do not significantly interfere with the intended function of any copolmyer employed as an AEA herein.

Other phosphonic-containing polymers include, for example, phosphonated ethylene having units of the formula.

$$-[CH_2)_{14}CHPO_3H_2]_n- \quad \text{V}$$

where n may for example be an integer or have a value giving the polymer a molecular weight of about 3,000; and sodium poly (butene-4,4-diphosphonate) having units of the formula:

$$-[CH_2-CH\text{-----}]- \quad \text{VI}$$
$$\quad\ \ \ \ \ \ \ \ \ \ \backslash$$
$$\quad\ \ \ \ \ \ \ \ \ \ CH_2-CH<(PO_3Na_2)_2 \quad \text{and}$$

poly (allyl bis (phosphonoethyl) amine) having units of the formula:

$$-[CH_2-CH\text{-----}]- \quad \text{VII}$$
$$\quad\ \ \ \ \ \ \ \ \ \ \backslash$$
$$\quad\ \ \ \ \ \ \ \ \ \ CH_2-N<(-C_2H_4PO_3H_2)_2$$

Other phosphonated polymers, for example poly (allyl phosphono acetate), phosphonated polymethacrylate, etc. and the geminal diphosphonate polymers disclosed in EP Publication 0321233 may be employed herein as AEA's, provided of course that they contain or are modified to contain the above-defined organic retention-enhancing groups.

The alpha- and beta-styrene phosphonic acid polymers and copolymers with other ethylenically unsaturated monomers may in general be prepared by heating the monomers or mixtures of monomers, preferably under nitrogen, in the presence of an effective amount, e.g. about 3-5%, of a radical initiator, e.g. AIBN, benzoyl peroxide, t-butyl hydroperoxide, persulfate or the like, neat or as solutions ion an inert solution such as acetonitrile, methylene chloride or 1,2-dichloromethane; at elevated temperatures, e.g. about 125° C. or at solvent reflux, for periods of about 8 to 200 hours. The crude polymeric products after removal of any inert solvent, is mixed with water and the aqueous mixture adjusted to a pH of about 8-10, e.g. with aqueous sodium hydroxide. After filtration of any solid impurities, the filtrate solution is dialyzed against water (e.g. at 3500 Dalton cutoff), and the purified polymer isolated from the retentate solution as by lyophylization.

According to another preferred embodiment, the AEA may comprise a synthetic anionic polymeric polycarboxylate. Although not used in the present invention to coact with polyphosphate anticalculus agent, synthetic anionic polymeric polycarboxylate having a molecular weight of about 1,000 to about 1,000,000, preferably about 30,000 to about 500,000, has been used as an inhibitor of alkaline phosphatase enzyme in optimizing anticalculus effectiveness of linear molecularly dehydrated polyphosphate salts, as disclosed in U.S. Pat. No. 4,627,977 to Gaffar et al. Indeed, in published British Patent Publication 22 00551, the polymeric polycarboxylate is disclosed as an optional ingredient in oral compositions containing linear molecularly dehydrated polyphosphate slats and noncationic antibacterial agent. It is further observed, in the context of the present invention that such polycarboxylate when containing or modified to contain retention-enhancing groups is markedly effective to enhance delivery and retention of the noncationic antibacterial, antiplaque agent to dental surfaces when another ingredient with which the polymeric polycarboxylate would coact (that is, molecularly dehydrated polyphosphate) is absent; for instance, when the ingredient with which the polymeric polycarboxylate coacts is especially the noncationic antibacterial agent.

Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. It is to be understood that the synthetic anionic polymeric polycarboxylates so disclosed in these several patents when containing or modified to contain the retention-enhancing groups defined above are operative as AEA's in the compositions and methods of this invention and such disclosures are to that extent incorporated herein by reference thereto.

These synthetic anionic polymeric polycarboxylates are often employed in the form of their free acids or preferably partially or more preferably fully neutralized water soluble or water-swellable (hydratable, gel forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, more preferably about 30,000 to about 500,000. These copolymers are available for example as Gantrez e.g. AN 139 (M.W. 500,000), A.N. 119 (M.W. 250,000); and preferably S-97 Pharmaceutical Grade (M.W. 70,000), of GAF Corporation.

Other AEA-operative polymeric polycarboxylates containing or modified to contain retention-enhancing groups include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103 M.W. 10,000 and EMA Grade 61, and 1:1 copolymers of acrylic acid with methyl or hydroxyethyl methacrylate, methyl or ethyl acrylate, isobutyl, isobutyl vinyl ether or N-vinyl-2-pyrollidone.

Additional operative polymeric polycarboxylates disclosed in above referred to U.S. Pat. Nos. 4,138,477 and 4,183,914, containing or modified to contain retention enhancing groups include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are retention-enhancing group-containing polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or a part of a terminal methylene grouping. Illustrative of such acids are acrylic, methacrylic, ethacrylic, alpha-chloroacrylic, crontonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomer copolymerizable with such carboxylic monomers include vinylacetate, vinyl chloride, dimethyl maleate and the like, Copolymers ordinarily contain sufficient carboxylic salt groups for water-solubility.

Also useful herein are so-called carboxyvinyl polymers disclosed as toothpast components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,904 to Harrison, and U.S. Pat. No. 3,711,604 to Colodney et al. They are commercially available for example under the trademarks Carbopol 934, 940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross linking agent, the cross-linked structure and cross-linkages providing the desired retention-enhancement by hydrophobicity and/or physical entrapment of the antibacterial agent or the like. Polycarbophil is somewhat similar, being polyacrylic acid cross-linked with less than 0.2% of divinyl glycol, the lower proportion, molecular weight and/or hydrophobicity of this cross-linking agent tending to provide little or no retention enhancement. 2,5-dimethyl-1,5-hexadiene exemplifies a more effective retention-enhancing cross-linking agent.

The synthetic anionic polymeric polycarboxylate component is most often a hydrocarbon with optional halogen and O-containing substituents and linkages as present in for example ester, ether and OH groups.

The AEA may also comprise natural anionic polymeric polycarboxylates containing retention-enhancing groups. Carboxymethyl cellulose and other binding agents gums and film-formers devoid of the above-defined delivery-enhancing and/or retention-enhancing groups are ineffective as AEA's.

As illustrative of AEA's containing phosphinic acid and/or sulfonic acid delivery enhancing groups, there may be mentioned polymers and copolymers containing units or moieties derived from the polymerization of vinyl or allyl phosphinic and/or sulfonic acids substituted as needed on the 1 or 2 (or 3) carbon atom by an organic retention-enhancing group, for example having the formula $-(X)_n-R$ defined above. Mixtures of these monomers may be employed, and copolymers thereof with one or more inert polymerizable ethylenically unsaturated monomers such as those described above with respect to the operative synthetic anionic polymeric polycarboxylates. As will be noted, in these and other polymeric AEA's operative herein, usually only one acidic delivery-enhancing groups is bonded to any given carbon or other atom in the polymer backbone or branch thereon. Polysiloxanes containing or modified to contain pendant delivery-enhancing groups and retention enhancing groups may also be employed as AEA's herein. Also effective as AEA's herein are ionomers containing or modified to contain delivery- and retention-enhancing groups. Ionomers are described on pages 546–573 of the Kirk Othmer Encyclopedia of Chemical Technology, third edition, Supplement Volume, John Wiley & Sons, Inc. copyright 1984, which description is incorporated herein by reference. Also effective as AEA's herein, provided they contain rare modified to contain retention-enhancing groups, are polyesters, polyurethanes and synthetic and natural polyamides including proteins and proteinaceous materials such as collagen, poly (argenine) and other polymerized amino acids.

Without being bound to a theory, it is believed that the AEA, especially polymeric AEA, is generally and desirably an anionic film forming material and is thought to attach to tooth surfaces and form a continuous film over the surfaces, thereby preventing bacterial attachment to tooth surfaces. It is possible that the non-cationic antibacterial agent forms a complex or other form of association with the AEA, thus forming a film of a complex or the like of the two over tooth surfaces. The film forming property of the AEA and the enhanced delivery property of the AEA and the enhanced delivery and retention of the antibacterial agent on tooth surfaces due to the AEA appears to make tooth surfaces unfavourable for bacterial accumulation particularly since the direct bacteriostatic action of the antibacterial agent controls bacterial growth. Therefore, through the combination of three modes of actions: 1) enhanced delivery, 2) long retention time on tooth surfaces, and 3) prevention of bacterial attachment to tooth surfaces the oral composition is made efficacious for reducing plaque. Similar antiplaque effectiveness is attained on soft oral tissue at or near the gum line.

In the oral preparation dentifrice, an orally acceptable vehicle including a water-phase with humectant is present. The humecant is preferably glycerine and/or sorbitol. Water is present typically in amount of at least about 3% by weight, generally about 3–35% and glycerine and/or sorbitol typically total about 6.5–75% by weight of the oral preparation dentifrice, more typically about 10–75%. Moreover, there is also present with the water-humectant vehicle a material which is particularly effective to dissolve the antibacterial agent in saliva, typically in amount of about 0.5–50% by weight. Together with this solubilizing material, the water-humectant phase typically amounts to about 10–80% by weight of the oral preparation dentifrice. Reference hereto to sorbitol refers to the material typically as available commercially in 70% aqueous solutions. Significant amounts of polyethylene glycol, particularly of molecular weight of 600 or more, should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of about 16 from that prevailing in the absence of the polyethylene glycol.

Materials which substantially dissolve the antibacterial agent, to permit its delivery to the soft oral tissues at or near the gumline, are employed in the present invention. Typical solubilizing materials include the humectant polyols such as propylene glycol, dipropylene glycol and hexylene glycol, cellosolves such as methyl cellosolve and ethyl cellosolve, vegetable oils and waxes containing at least about 12 carbon atoms in a straight chain such as olive oil, castor oil, and petrolatum and esters such as amyl acetate, ethyl acetate, glyceryl tristearate and benzyl benzoate. Propylene glycol is preferred. As used herein, "propylene glycol" includes 1,2-propylene glycol and 1,3-propylene glycol.

When the amount of substantially water-insoluble noncationic antibacterial agent is low, say up to about 0.3% by weight, as little as about 0.5% by weight of the solubilizing agent can be sufficient to solubilize the antibacterial agent. When higher amounts such as at least about 0.5% by weight, of antibacterial agent are present, it is desirable that at least about 5% by weight, typically up to about 20% or more by weight, of the solubilizing agent be present.

The pH of oral preparation dentifrice of the invention is generally in the range of about 4.5 to about 9 or 10 and preferably about 6.5 to about 7.5. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In this invention, the oral composition dentifrice may be substantially gel in character, such as a gel dentifrice. Such gel oral preparations generally contain siliceous dentally acceptable polishing material. Preferred polishing materials include crystalline silica having particle sized of up to about 5 microns, a mean particle size of up to about 1.1 microns, and a surface area of up to about 50,000 cm.$^2$/gm., silica gel or colloidal silica and complex amorphous alkali metal aluminosilicate.

When visually clear or opacified gels are employed, a polishing agent of colloidal silica, such as those sold under the trademark SYLOID as Syloid 72 and Syloid 74 or under the trademark SANTOCEL as Santocel 100 or alkali metal aluminosilicate complexes (that is, silica containing alumina combined in its matrix) are particularly useful, since they are consistant with gel-like texture and have refractive indices close to the refractive indices of gelling agent-liquid (including water and/or humectant) systems commonly used in dentifices.

The polishing material is generally present in the oral composition dentifrices such as toothpaste cream paste or gel compositions in weight concentrations of about 5% to about 30%.

In a gel toothpaste, the liquid vehicle may typically comprise about 3-35% by weight of water, such as about 10-35%, and humectant in an amount ranging from about 6.5% to about 80%, such as about 10% to about 80% by weight of the preparation. In clear gels where the refractive index is an important consideration, about 3-30% of water, 0 to about 70% of glycerine and about 20-25% of sorbitol are preferably employed. The solubilizing material, typically present in amount of about 0.5-20% or more by weight, may be considered to be a part of the liquid vehicle in the oral preparation dentifrice as prepared. As indicated, the solubilizing materials include polyol humectants such as propylene glycol and dipropylene glycol.

The oral composition dentifrices typically contain a natural or synthetic thickener or gelling agent in proportions of about 0.1 to about 10%, preferably about 0.5 to about 5%. A suitable thickener is synthetic hectorite, a synthetic colloidal magnesium alkali metal silicate complex clay available for example as Laponite (e.g. CP, SP 2002,/D) marked by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable gelling agents or thickeners include Irish moss, i-carrageenan, gum tragacanth, starch, polyvinylpyrrolidone, hydroxyethypropyl cellulose, hydroxybutyl methyl cellulose, hydroxypropyl methyl cellulose, hydroxyethyl cellulose (e.g. available as Natrosol), sodium carboxymethyl cellulose, and colloidal silica such those available as finely round Syloid 244 and Sylodent 15.

Since there maybe a tendency for the dentifrice to separate into liquid and solid portions when about 5% by weight or more of the solubilizing material such as propylene glycol is present and since excellent antiplaque effects can be obtained with small amounts of antibacterial agent which do not require so much solubilizing humectant to effect solubilization, a preferred dentifrice contains about 0.25-0.35%, say about 0.3%, by weight of the antibacterial agent, about 1.5-2% by weight of the polycarboxylate and about 0.5%-1% by weight of the solubilizing material.

Without being bound to a theory whereby the advantages of this invention are achieved, it is believed than an aqueous, humectant vehicle is normally solubilized in surfactant micelles in the mobile phase (that is, not including gelling agent and polishing agent) of a dentifrice formula. The phase solution of dentifrice during use becomes diluted with saliva which causes triclosan to precipitate. However, the solubilizing material of the present invention permits the antibacterial agent to remain in solution in the mobile phase in the presence of saliva and to effectively reach the soft oral tissues. Propylene glycol being a strong solubilizing humectant for triclosan, appears to prevent its precipitating and permit its continued presence within the mobile phase. In this regard it is noted that propylene glycol is widely used in drug delivery systems (for instance in European Patent Publication 271,332) for its strong interaction with biological membranes. It may be that in the oral cavity, triclosan is partitioned from the aqueous environment oral preparation into propylene glycol-surfactant emulsion and further that propylene glycol in the bulk mobile phase allows greater probability of triclosan emergence out of surfactant micelles, thereby rendering triclosan available for delivery into bacterial and soft surfaces as well as onto tooth surfaces. Similar remarks apply to other water-insoluble noncationic antibacterial agents herein described.

The oral composition dentifrice may also contain a source of fluoride ions, or fluorine-providing component, as anti-caries agent, in an amount sufficient to supply about 25 ppm to 5,000 ppm of fluoride ions. This compound may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example, sodium fluoride, potassium fluoride, ammonium fluoride, calcium fluoride, a copper fluoride such as cuprous fluoride, zinc fluoride, barium fluoride, sodium flourosilicate, ammonium flourosilicate, sodium fluorozirconate, sodium fluorozirconate, sodium monofluorphosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, e.g. dental gel, an amount of such compound which releases up to about 5,000 ppm of F ion by weight of the preparation is considered satisfactory. Any suitable minimum amount of such compound may be used, bu tit is preferably to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1–3%, more typically about 0.76%.

It will be understood that, as is conventional, oral preparations are to be sold or otherwise distributed in suitable labelled packages. Thus a dentifrice gel will usually be in a collapsible tube, typically aluminum, lined lead or plastic, or other squeeze, pump or pressurized dispenser for metering out the contents, having a label describing it, in substance, as a dentifrice gel or the like.

Organic surface-active agents are used in the compositions of the present invention to achieve increased prophylactic action, assist in achieving thorough and complete dispersion of the antiplaque antibacterial agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium slat of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of abut 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monosterate) and polypropyleneoxide (e.g. Pluronic materials).

Surface active agent is typically present in amount of about 0.5–5% by weight, preferably about 1–2.5%. It is noteworthy, that surface active agent may assist in the dissolving of the noncationic antibacterial agent and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials which are generally soluble and which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine, methyl ester), saccharine and the like. Suitable, flavor and sweetening agents may each or together comprise from about 0.1% to 5% more of the preparation. Moreover, flavor oil is believed to aid the dissolving of the anti-bacterial agent.

In the preferred practice of this invention an oral composition dentifrice containing the composition of the present invention is preferably applied regularly to dental enamel and soft oral tissues, particularly at or near the gum line, such as every day or every second or third day or preferably from 1 to 3 times daily, at a pH of about 4.5 to about 9, generally about 5.5 to about 8, preferably about 6.5 to 7.5, for at least 2 weeks up to 8 weeks or more up to lifetime.

The composition of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plastizers or softeners, sugar or other sweeteners or carbohydrates such as glucose, sorbitol and the like.

EXAMPLE A

Poly (Beta-styrenephosphonic Acid)

A mixture of 18.1 g. (0.1M) of beta-styrenephosphonic acid and 0.82 g. (0.005M) of azobisisobutyronitrile (AIBN) in 300 ml. of anhydrous acetonitrile is stirred under reflux under dry nitrogen for 96 hrs. The mixture is cooled and the crude product precipitate is isolated by filtration, washed with acetonitrile, and air dried. The crude product is dissolved in aqueous sodium hydroxide (to pH 11) and dialyzed against water at 3000 Dalton cutoff. The retentate solution is reduced to 100 ml., in vacuo, and freeze-dried to yield the purified product polymer as a white powdery solid in 0.91 g. yield. Infrared spectrum: 1610, 1550, 745 cm$^{-1}$ (aryl,5 adjacent H); 1240, 1020, 950 cm$^{-1}$ (phosphonate). Proton nmr ($D_2O$): tr,6.4 ppm. (H on carbon bearing phosphonate); m,7.3 ppm. (aryl and benzylic protons); area ration 1 to 6. Phosphorus nmr ($D_2O$): m,6.2 ppm. (alkyl phosphonate).

EXAMPLE B

Copoly (Beta-styrenephosphonic Acid/Vinylphosphonic Acid)

A mixture of 10.68 g. (0.058M) of beta-styrenephosphonic acid, 6.0 ml. (8.4 g, 0.058M) of vinylphosphonyl dichloride, and 0.5 g. of AIBN is heated, with stirring, under an anhydrous nitrogen atmosphere intermittently for a few hours, then overnight at 80°–90° C. The material is transferred to a beaker with 60–70 ml. of water. A crystalline precipitate forms as the warm solution cools. The mixture is filtered, the aqueous filtrate is diluted to 125 ml. with water, and the resulting solution is dialyzed vs. water at 3500 Dalton cutoff. The retentate solution is evaporated in vacuo to give 0.600 g. purified acid form of the copolymer. Proton nmr ($D_2O$) shows two broad regions at 1.0–2.8 (alkyl, 11 H) and 6.9–7.5 ppm. (aryl, 5 H). These data indicate a ratio of beta-styrenephosphonic acid to vinylphosphonic acid of 1:3 in the copolymer. Phosphorus nmr ($D_2O$) shows two main phosphorus signals centered at about 23.4 and 29.2 ppm. respectively.

EXAMPLE C

Poly (Alpha-styrenephosphonic Acid)

A mixture of 2.21 g. (0.01M) of alpha-styrenephosphonyl dichloride and 0.01 g. of AIBN is stirred under a nitrogen atmosphere at 115° C. At 12 hour intervals, successive 0.01 g. AIBN portions are added to the mixture. After 96 hours, the mixture is allowed to cool and dissolved in water. The pH is adjusted to 8–10 with aq. sodium hydroxide in a total volume of 125 ml. The solution is filtered and the filtrate is dialyzed against water in a 3500 Dalton cutoff cellulose bag. The retentate is reduced to about 50 ml. in vacuo, then freeze dried. The polymer is obtained as a tan powdery solid in 0.08 g. yield. Proton nmr ($D_2O$): 7.2–7.4 ppm. (m, phenyl). Phosphorus nmr ($D_2O$): 23–25 ppm. (m).

The following examples are further illustrative of the nature of the present invention, but it is understood that the invention is not limited thereto. All amounts and proportions referred to herein and in the appended claims are by weight, unless otherwise indicated.

EXAMPLE 1

The effect of synthetic anionic linear polycarboxylate on the uptake, retention to and release from tooth surfaces of water-insoluble noncationic antibacterial agent is asses in vitro on a saliva coated hydroxyapatite disk and on exfoliated buccal epithelial cells. The in vitro assessments are correlatable to in viva delivery, and retention on oral surfaces.

For the test of delivery of antibacterial agent to a saliva coated hydroxyapatite disk, hydroxyapatite (HA) obtained from the Monsanto Co. is washed extensively with distilled water, collected by vacuum filtration, and permitted to dry overnight at 37° C. The dried HA is ground into a powder with a mortar and pestle. 150.00 mgs of HA are placed in the chamber of a KBr pellet die (Barnes Analytical, Stanford, Conn.). and compressed for 6 minutes at 10,000 pound in a Carver Laboratory press. The resulting 13 mm disks are sintered for 4 hours at 800° C. in a Thermolyne furnace. Parafilm stimulated whole saliva is collected into an ice-chilled glass beaker. The saliva is clarified by centrifugation at 15,000 Xg (times gravity) for 15 minutes at 4° C. Sterilization of the clarified-saliva is done at 4° C. with stirring by irradiation of the sample with UV light for 1.0 hour.

Each sintered disk is hydrated with sterile water in a polyethylene test tube. The water is then removed and replaced with 2.00 ml of saliva. A salivary pellicle is formed by incubating the disk overnight at 37° C. with continuous shaking in a water bath. After this treatment, the saliva is removed and the disks are treated with 1.00 ml of a solution containing antibacterial agent (Triclosan) dentifrice liquid phase solution and incubated at 37° C. with continuous shaking in the water bath. After 30 minutes, the disk is transferred into a new tube and 5.00 ml of water are added followed by shaking the disk gently with a Vortex. The disk is then transferred into a new tube and the washing procedure repeated twice. Finally, the disk is transferred carefully into a new tube to avoid co-transfer of any liquid along with the disk. Then 1.00 ml of methanol is added to the disk and shaken vigorously with a Vortex. The sample is left at room temperature for 30 minutes to extract adsorbed Triclosan into the methanol. The methanol is then aspirated and clarified by centrifugation in a Beckman Microfuge 11 at 10,000 rpm to 5 minutes. After this treatment, the methanol is transferred into HPLC (high performance liquid chromatography) vials for determination of antibacterial agent. Triplicate samples are used in all experiments.

For the test of retention of antibacterial agent to a saliva coated HA disk, a saliva coated HA disk is treated with dentifrice slurries as described above. After incubation for 30 minutes at 37° C., the HA disk is removed from the dentifrice slurry, washed twice with water, and then reincubated with parafilm stimulated human whole saliva which had been clarified by centrifugation. After incubation at 37° C. with constant shaking for various periods, the HA disk is removed from the saliva, and the amount of antibacterial agent (Triclosan) retained onto the disk and released into saliva is determined by analytical method using HPLC.

For the assay of delivery of antibacterial agent to buccal epithelial cells, the delivery is measured in order to determine the effect of PVM/MA on the delivery of antibacterial agent (Triclosan) to soft oral tissue from a dentifrice product. Buccal epithelial cells are collected with a wooden applicator stick by gently rubbing the oral mucosa. The cells are suspended in Resting Saliva Salts (RSS) Buffer (50 mM NaCl, 1.1 mM $CaCl_2$, and 0.6 mM $KH_2PO_4$ pH 7.0) to 5–6×10$^5$ cells/ml using a hemocytometer to enumerate the cells and kept in ice until use. 0.5 ml of cell suspension, preincubated to 37° C. in a waterbath, is added with 0.5 ml of the test antibacterial agent solution and incubated at 37° C. The antibacterial agent solution in the incubation mixture is diluted at least 10 times in order to lower the surfactant concentration and prevent destruction of cell membranes by the surfactant. After 30 minutes of incubation, the cells are harvested by centrifugation in Beckman Microfuge 11 at 5,000 rpm for 5 minutes. The cells, collected as the pellet, are washed 3 times with RSS buffer and treated with 1.5 ml of methanol. The sample is mixed vigorously by Vortex and then centifuged as described above. The supernatant is analyzed for antibacterial agent by the HPLC method.

Dentifrices are prepared having the following formulas:

|  | Parts | |
| --- | --- | --- |
|  | A | B |
| Propylene Glycol (1,2) | 10.00 | 10.00 |
| Iota Carrageenan | 0.75 | 0.75 |
| Gantrez S-97 | — | 2.00 |
| Titanium Dioxide | 0.50 | 0.50 |
| Sorbitol (70%) | 30.00 | 30.00 |
| Sodium Fluoride | 0.332 | 0.332 |
| Sodium Saccharin | 0.40 | 0.40 |
| Silica Thickener (Sylodent 15) | 3.00 | 3.00 |
| Silica Polishing Agent (Zeodent 113) | 20.00 | 20.00 |
| Triclosan | 0.20 | 0.20 |
| Sodium Lauryl Sulfate | 2.00 | 2.00 |
| Flavor Oil | 0.95 | 0.95 |
| Ethyl Alcohol | 1.00 | 1.00 |
| Sodium Hydroxide (50%) | 0.80 | 0.80 |
| Water | Q.S. to 100.0 | Q.S. to 100.0 |

The uptake of triclosan on the saliva coated hydroxyapatite disk and on buccal epithelial cells with and without the polymeric polycarboxylate, Gantrez S-97, is set forth in Table 1 below:

TABLE 1

| Dentifrice | Uptake of Triclosan in micrograms On Saliva Coated Disk | In Micrograms × 10$^5$ Buccal Epithelial Cells |
| --- | --- | --- |
| A | 25.0 | 38.0 |
| B | 54.0 | 96.0 |

These results reveal that the Gantrez material (present in Dentifrice B) greatly enhances the delivery and uptake of triclosan to saliva coated hydroxyapatite disk and to the exfoliated buccal epithelial cells.

Similar results are obtained when the dentifrices contain 0.30 parts of tricolosan.

EXAMPLE 2

In tests with saliva coated hydroxapatite disks and exfoliated buccal epithelical cells different from those set forth in Example 1 above, said dentifrice B containing 2.00% Gantrez S-97 and 0.20% of triclosan, 10.00% of propylene glycol and 2.00% of sodium lauryl sulfate and an equivalently formulated Dentifrice (B'), except for the presence of 0.30% of triclosan were compared with a commercially available Dentifrice (C) containing hydrated alumina polishing agent and (a) 0.2% of triclosan, (b) no Gantrez material, (c) no propylene glycol, (d) 0.5% zinc citrate, (e) 2.5% of surface active agents (f) sodium monofluorophosphate and hydrated alumina polishing agent; and the dentifrice formulation below (C') which is similar to commercial Dentifrice C except for the presence of 0.30% of triclosan:

| DENTIFRICE C' | |
| --- | --- |
|  | % |
| Sorbitol (70%) | 27.00 |
| Sodium Carboxymethyl Cellulose | 0.80 |
| Sodium Monofluorophosphate | 0.85 |
| Zinc Citrate | 0.50 |
| Sodium Saccharin | 0.18 |
| Water | 16.47 |
| Hydrated Alumina Polishing Agent | 50.00 |
| Ethanol | 0.20 |
| Sodium Lauryl Sulfate | 1.875 |
| Sodium Dodecyl Benzene Sulfonate | 0.625 |
| Triclosan | 0.30 |
| Flavor | 1.20 |

Since Dentifrices C and C' contain a total of 2.50% of surface active agent, more surface active agent is available to dissolve triclosan than in Dentifrices B and B' which contain 2.00%. However, propylene glycol present in siliceous polishing agent Dentifrices B and B' (but not in hydrated alumina polishing agent Dentifrices C and C') insures optimum dissolution of triclosan.

The advantage of Dentifrices B and B' (containing propylene glycol) and Gantrez) over Dentifrices C and C' in triclosan uptake on saliva coated hydroxyapatite disks and on exfoliated buccal epithelial cells is shown in the Table 2 below:

TABLE 2

| | Delivery to Triclosan | |
| --- | --- | --- |
| Dentifrice | To Saliva Coated Hydroxyapatite Disk (in micrograms) | To Buccal Epithelial Cells in micrograms × 10$^6$ Epithelial Cells |
| B | 41.1 | 101.6 |
| B' | 77.4 | 142.0 |
| C | 20.4 | 61.0 |
| C' | 42.6 | 100.0 |

Additional experiments with Dentifrice B' (0.3% Triclosan; Gantrez; Propylene Glycol) in a 50% slurry of the dentifrice to determine the retention of triclosan on the saliva coated hydroxyapatite disk over a period of time reveals retention of excellent levels of triclosan as shown in Table 3 below:

TABLE 3

| Retention of Triclosan Adsorption from Dentifrice Slurry | |
| --- | --- |
| Time (in Minutes) | Retention of Triclosan (Micrograms/Disk) |
| 0 | 70 |
| 30 | 60 |
| 60 | 70 |
| 120 | 65 |
| 180 | 57 |
| 240 | 59 |

These results indicate that dentifrices containing triclosan, Gantrez material and propylene glycol can provide enhanced delivery of triclosan to, and retention on, tooth surfaces and soft surfaces in the oral cavity, thereby providing improved antiplaque and antibacterial effects.

EXAMPLE 3

For purpose of comparison formulas a and b below are prepared

|  | Dentifrice | |
| --- | --- | --- |
|  | a | b |
|  | % | |
| Glycerin | 10.00 | — |
| Propylene Glycol | — | 10.00 |
| Iota Carrageenan | 0.60 | 0.60 |
| Sorbitol (70%) | 25.00 | 25.00 |
| Sodium Saccharin | 0.40 | 0.40 |
| Sodium Fluoride | 0.243 | 0.243 |
| Titanium Dioxide | 0.50 | 0.50 |
| Gantrez S-97 | 2.00 | 2.00 |
| Water | 29.157 | 29.157 |
| NaOH (50%) | 2.00 | 2.00 |
| Zeodent 113 (Silica Polishing Agent) | 20.00 | 20.00 |
| Sylodent 15 (Silica Thickener) | 5.50 | 5.50 |
| Flavor | 1.10 | 1.10 |
| Triclosan | 0.50 | 0.50 |
| Sodium Lauryl Sulfate | 2.00 | 2.00 |
| Ethanol | 1.00 | 1.00 |

Formula a is a dentifrice containing a Gantrez polycarboxylate, with triclosan as an antibacterial antiplaque agent and no solublizing agent. In Formula b, propylene glycol solubilizing agent is present.

Formula a ia poor in delivery of triclosan on buccal epithelial cells while Formula b is markedly effective.

The foregoing results reveal excellent delivery of Triclosan dentifrice.

EXAMPLE 4

An "in-house" study was conducted on a group of volunteers to assess the effects of particular dentifrices in influencing plaque regrowth in accordance with the method described by Addy, Willis and Moran, J. Clin. Perio., 1983, Vol. 10, Pages 89–99. The dentifrices tested included a placebo control containing no triclosan (i) and a dentifrice in accordance with this invention containing 0.3% of triclosan, 10% propylene glycol (instead of 3% polyethylene glycol 600) and 2% of Gantrez S-97 and humectant of propylene glycol and sorbitol (ii). The formulas of the dentifrices are as follows:

|  | Parts | |
| --- | --- | --- |
|  | (i) Placebo | (ii) Invention |
| Polyethylene Glycol 600 | 3.00 | — |
| Glycerine | 25.00 | — |
| Propylene Glycol | — | 10.00 |
| Sorbitol (70%) | 41.617 | 25.00 |
| Sodium Carboxymethyl Cellulose | 0.35 | — |
| Iota Carrageenan | — | 0.60 |
| Sodium Benzoate | 0.50 | — |
| Sodium Saccharin | 0.20 | 0.40 |
| Sodium Fluoride | 0.243 | 0.243 |
| Silica Polishing Agent (Zeodent 113) | 18.00 | 20.00 |
| Silica thickener (Sylox 15) | 5.50 | 5.50 |
| Water | 3.00 | 28.757 |
| Gantrez S-97 | — | 2.00 |
| Triclosan | — | 0.30 |
| Titanium Dioxide | 0.50 | 0.50 |
| Sodium Lauryl Sulfate | 1.20 | 2.50 |
| Flavor | 0.89 | 1.10 |
| Ethyl Alcohol | — | 1.00 |
| Sodium Hydroxide (50%) | — | 2.00 |

With regard to plaque reduction, on the teeth of the volunteers, compared to placebo (i), invention (ii) provided a significant decrease of 20%.

Since lesser amounts of propylene glycol can dissolve the 0.3% of triclosan present in Toothpaste (ii), similar results are expected when the amount of propylene glycol is reduced to 0.5 parts and the amount of sorbitol is increased to 39.5 parts. Likewise, the other solubilizing materials dipropylene glycol, hexylene glycol, methyl cellosolve, ethyl cellosolve, olive oil, castor oil, petrolatum, amyl acetate, ethyl acetate, glyceryl tristearate and benzyl benzoate, in place of propylene glycol, can effectively deliver triclosan to soft oral tissues.

EXAMPLE 5

The following dentifrices of the invention are prepared:

|  | Parts | |
| --- | --- | --- |
|  | A | B |
| Glycerine | — | 20.00 |
| Propylene Glycol | 10.00 | 0.50 |
| Sorbitol (70%) | 25.00 | 19.50 |
| Sodium Carboxymethyl Cellulose | — | 1.10 |
| Iota Carrageenan | 0.600 | — |
| Sodium Saccharin | 0.40 | 0.30 |
| Sodium Fluoride | 0.243 | 0.243 |
| Silica Polishing Agent (Zeodent 113) | 20.00 | 20.00 |
| Silica thickener (Sylox 15) | 5.50 | 3.00 |
| Water | 28.757 | 15.307 |
| Gantrez S-97 | 2.00 | 2.00 |
| Triclosan | 0.50 | 0.30 |
| Titanium Dioxide | 0.50 | 0.50 |
| Sodium Lauryl Sulfate | 2.50 | 2.00 |
| Flavor | 1.10 | 0.95 |
| Ethanol | 1.00 | — |
| Sodium Hydroxide (50%) | 2.00 | 1.60 |

In the foregoing examples, improved results may also be obtained by replacing triclosan with other antibacterial agents herein described such as phenol, thymol, eugenol and 2,2'-methylene bis (4-chloro-6-bromophenol) and/or by replacing Gantrez with other AEA's such as a 1:1 copolymer of maleic anhydride and ethyl acrylate, sulfoacrylic oligomers, Carbopols (e.g. 934), polymers of monomeric alpha- or beta-styrene phosphonic acid and copolymers of these styrene phosphonic acid monomers with each other or with other ethylenically unsaturated polymerizable monomers such as vinyl phosphonic acid.

EXAMPLE 6

The following liquid phase dentifrice solutions are tested for uptake and retention of triclosan on saliva coated HA disks following the test procedures described in Example 1 with the indicated results:

|  | Parts | | | |
| --- | --- | --- | --- | --- |
| Ingredients | A | B | C | D |
| Sorbitol (70% solution) | 30.0 | 30.0 | 30.0 | 30.0 |
| Glycerol | 9.5 | 9.5 | 9.5 | 9.5 |
| Propylene Glycol | 0.5 | 0.5 | 0.5 | 0.5 |
| SLS | 20.0 | 20.0 | 20.0 | 20.0 |
| NaF | 0.243 | 0.243 | 0.243 | 0.243 |
| Flavor Oil | 0.95 | 0.95 | 0.95 | 0.95 |
| Triclosan | 0.3 | 0.3 | 0.3 | 0.3 |
| Water | 56.507 | 54.507 | 54.507 | 54.507 |
| Poly (beta-styrenephosphonic acid) |  | 2.0 |  |  |
| Poly (alpha-styrenephosphonic acid) |  |  | 2.0 |  |

-continued

| Ingredients | Parts | | | |
|---|---|---|---|---|
| | A | B | C | D |
| Polyvinyl Alcohol | | | | 2.0 |
| Adjusted to pH 6.5 with NaOH | 31.0 | 174.0 | 86.0 | 36.0 |
| Triclosan Uptake in Micrograms on Saliva Coated Disks | | | | |
| Retention of Triclosan on Saliva Coated HA Disks After: | | | | |
| Initial | | 183.0 | | |
| 30 minutes | | 136.0 | | |
| 1 hour | | 105.0 | | |
| 3 hours | | 83.0 | | |

The above results show that solution (D) containing polyvinyl alcohol, not an AEA hereunder, produced a triclosan uptake of only 36.0, quite similar to the 31.0 uptake of the control solution (A) without additive. In contrast, solution (C) with poly (alpha-styrenephosphonic acid) produces an uptake of 86.0, more than double that of solutions (A) and (D), and solution (B) with poly (beta-styrenephosphonic acid) produces an uptake about 5 times that of solutions (A) and (D), tending to indicate further that vicinal substitution of the delivery-enhancing group yields superior results. The above results also show the surprisingly good retention of triclosan on the HA disks over time obtained with solution (B) containing poly (beta-styrenephosphonic acid) (M.W's about 3,000 to 10,000).

This invention has been described with respect to certain preferred embodiments and it will be understood that modifications and variations thereof obvious to those skilled in the art are to be included within the spirit and purview of this application and the scope of the appended claims.

We claim:

1. In a method of preparing an oral composition dentifrice wherein delivery and retention of a plaque-inhibiting antibacterial agent is enhanced by attaching, adhering or bonding to oral tooth and gum surfaces, comprising an orally acceptable aqueous vehicle, about 5-30% by weight of a siliceous polishing agent and an effective amount in the range of about 0.01-5% by weight of substantially water insoluble noncationic antibacterial agent, the improvement comprising employing in said composition about 0.5-50% by weight of a solubilizing material for said antibacterial agent in amount sufficient to dissolve said antibacterial agent in saliva and permit delivery of said antibacterial agent to soft oral tissues at or near the gum line, and about 0.05-5% by weight of a water-soluble or swellable antibacterial-enhancing agent, which contains at least one delivery-enhancing functional group and at least one organic retention-enhancing group, which delivery-enhancing group enhances delivery of said antibacterial agent to oral tooth and gum surfaces and said retention-enhancing group enhances attachment, adherence or bonding of said antibacterial agent on oral tooth and gum surfaces.

2. In method of attaching, adhering or bonding a plaque-inhibiting antibacterial agent to oral tooth and gum surfaces comprising applying to oral tooth and gum surfaces comprising applying to oral surfaces an oral composition dentifrice comprising an orally acceptable aqueous vehicle, about 5-30% by weight of a siliceous polishing agent, an effective amount in the range of about 0.01-5% by weight of substantially water insoluble noncationic antibacterial agent, the improvement which comprises employing in said composition about 0.5-50% by weight of a solubilizing material for said antibacterial gent in amount sufficient to dissolve said antibacterial agent in saliva and permit delivery of said antibacterial agent to soft oral tissues at or near the gum line and an effective amount in the range of about 0.05-5% by weight of an antibacterial-enhancing agent which contains at least one delivery-enhancing functional group and at least one organic retention-enhancing group, which delivery-enhancing group enhances delivery of said antibacterial agent to oral tooth and gum surfaces and said retention-enhancing group enhances attachment, adherence or bonding of said antibacterial agent on oral tooth and gum surfaces.

3. The method claimed in either of claims 1 or 2 wherein said antibacterial agent is selected from the group consisting of halogenated diphenyl ethers, halogenated salicylanilides, benzoic esters, halogenated carbanilides and phenolic compounds.

4. The method claimed in claim 3 wherein said antibacterial agent is a halogenated diphenyl ether.

5. The method claimed in claim 4 wherein said halogenated diphenyl ether is 2,4,4'-trichloro-2'-hydroxydiphenyl ether.

6. The method claimed in either of claims 1 or 2 wherein said amount of antibacterial agent is about 0.25-0.5%.

7. The method claimed in either of claims 1 or 2 wherein said solubilizing material is selected from the group consisting of propylene glycol, dipropylene glycol, hexylene glycol, methyl cellosolve, ethyl cellosolve, vegetable oil and wax containing at least about 12 carbon atoms, amyl acetate, ethyl acetate, glycerol tristearate and benzyl benzoate.

8. The method claimed in claim 7 wherein said solubilizing agent is propylene glycol.

9. The method claimed in either of claims 1 or 2 wherein said antibacterial-enhancing agent has an average molecular weight of about 100 to about 1,000,000.

10. The method claimed in claim 9 wherein said delivery enhancing group is acidic.

11. The method according to claim 10 wherein said delivery-enhancing group is selected form the group consisting of carboxylic, phosphonic, phosphinic, and sulfonic acids, and their salts, and mixtures thereof and wherein said organic retention-enhancing group comprises the formula —(X)$_n$—R wherein X is O, N, S, SO, SO$_2$, P, PO or Si, R is hydrophobic alkyl, alkenyl, acyl, aryl, alkaryl, aralkyl, heterocyclic, or their inert-substituted derivatives, and n is zero or 1 or more and wherein said antibacterial enhancing agent is a natural or synthetic polymerizable monomer or a polymer selected from the group consisting of oligomers, homopolymers, copolymers of two or more monomers, ionomers, block copolymers, graft copolymers and cross-linked polymers and monomers.

12. The method claimed in claim 11 wherein said antibacterial-enhancing agent is an anionic polymer containing a plurality of said delivery-enhancing and retention-enhancing groups.

13. The method claimed in claim 12 wherein said anionic polymer comprising a chain containing repeating units each containing at least one carbon atom.

14. The method claimed in claim 13 wherein each unit contains at least one delivery-enhancing group and at least one organic retention-enhancing group bonded to the same or vicinal, or other atoms in the chain.

15. The method claimed in claim 11 wherein the delivery-enhancing group is a carboxylic group or salt thereof.

16. The method claimed in claim 15 wherein the antibacterial-enhancing agent is a copolymer of maleic acid or anhydride with another ethylenically unsaturated polymerizable monomer.

17. The method claimed in claim 16 wherein said other monomer of said copolymer is methyl vinyl ether in a 4:1 to 1:4 molar ratio with the maleic acid or anhydride.

18. The method claimed in claim 17 wherein said copolymer has a molecular weight of about 30,000–1,000,000 and is present in amount of about 0.1–2% by weight.

19. The method claimed in claim 18 wherein the copolymer has an average molecular weight of about 70,000.

20. The method claimed in either of claims 1 or 2 wherein said oral composition contains an effective anticaries amount of a fluoride ion-providing source.

* * * * *